United States Patent
Aoki et al.

(10) Patent No.: US 12,201,709 B2
(45) Date of Patent: Jan. 21, 2025

(54) HYDROXYAPATITE, COSMETIC, FOOD, AND METHOD FOR PRODUCING THE SAME

(71) Applicant: Brainy Inc., Naha (JP)

(72) Inventors: Hideki Aoki, Tokyo (JP); Nobukiyo Tanaka, Urasoe (JP)

(73) Assignee: Brainy Inc., Naha (JP)

( * ) Notice: Subject to any disclaimer, the term of this patent is extended or adjusted under 35 U.S.C. 154(b) by 210 days.

(21) Appl. No.: 17/689,042

(22) Filed: Mar. 8, 2022

(65) Prior Publication Data

US 2022/0192943 A1    Jun. 23, 2022

Related U.S. Application Data (60) Division of application No. 16/665,582, filed on Oct. 28, 2019, now abandoned, which is a continuation of application No. PCT/JP2017/016855, filed on Apr. 27, 2017.

(51) Int. Cl.

| | |
|---|---|
| *A61K 8/24* | (2006.01) |
| *A23C 9/13* | (2006.01) |
| *A23L 2/02* | (2006.01) |
| *A23L 2/52* | (2006.01) |
| *A23L 33/16* | (2016.01) |
| *A61K 8/04* | (2006.01) |
| *A61Q 19/00* | (2006.01) |
| *A61Q 19/10* | (2006.01) |
| *C01B 25/16* | (2006.01) |

(52) U.S. Cl.
CPC .............. *A61K 8/24* (2013.01); *A23C 9/1322* (2013.01); *A23L 2/02* (2013.01); *A23L 2/52* (2013.01); *A23L 33/16* (2016.08); *A61K 8/04* (2013.01); *A61Q 19/00* (2013.01); *A61Q 19/10* (2013.01); *C01B 25/16* (2013.01); *A23V 2002/00* (2013.01); *C01P 2002/50* (2013.01); *C01P 2004/64* (2013.01)

(58) Field of Classification Search
None
See application file for complete search history.

(56) References Cited

U.S. PATENT DOCUMENTS

| | | |
|---|---|---|
| 6,585,946 B1 | 7/2003 | Bonfield et al. |
| 2002/0127260 A1 | 9/2002 | Riman et al. |
| 2005/0186249 A1 | 8/2005 | Riman et al. |
| 2005/0271571 A1 | 12/2005 | Godber et al. |
| 2008/0199382 A1 | 8/2008 | Martinetti et al. |
| 2009/0130150 A1 | 5/2009 | Gazzaniga et al. |
| 2009/0130444 A1 | 5/2009 | Godber et al. |
| 2010/0331168 A1 | 12/2010 | Riman et al. |
| 2016/0235683 A1 | 8/2016 | Powell et al. |

FOREIGN PATENT DOCUMENTS

| | | |
|---|---|---|
| CN | 101489925 A | 7/2009 |
| CN | 105722504 A | 6/2016 |
| FR | 2869893 A1 | 11/2005 |
| JP | 62-195317 A | 8/1987 |
| JP | 63-096110 A | 4/1988 |
| JP | 2001-526169 A | 12/2001 |
| JP | 2004532172 A | 10/2004 |
| JP | 2008-501643 A | 1/2008 |
| JP | 2009-501596 A | 1/2009 |
| JP | 2014-532671 A | 12/2014 |
| JP | 2016-537408 A | 12/2016 |

OTHER PUBLICATIONS

Suchanek, et al., Mechanochemical-hydrothermal Synthese of Calcium Phosphate Powders and Coupled Magnesium and Carbonate Substitute, Journal of Solid State Chemistry (2004) pp. 793-799, (7 pages).

Khan, et al., Microwave Assisted Synthesis and Characterization of Magnesium Substituted Calcium Phosphate Bioceramics, Material Science and Engineering C56 (2015) ) pp. 286-291 (8 pages).

Sader, et al. Simultaneous Incorporation of Magnesium and Carbonate in Apatite: Effect on Physico-chemical Properties, Materials Research, 2013: 16(4); pp. 779-784 (6 pages).

International Search Report for Patent Application No. PCT/JP2017/016855 dated Aug. 1, 2017 (16 pages).

First Office Action for corresponding Chinese Application No. 201780090083.X dated Jun. 13, 2022, with English translation (25 Pages).

*Primary Examiner* — Nannette Holloman (74) *Attorney, Agent, or Firm* — Harness, Dickey & Pierce, P.L.C.

(57) ABSTRACT

According to the present invention, provided is a carbonate- and magnesium-substituted hydroxyapatite having a particle size of 5 nm or more and 60 nm or less, wherein a portion of the calcium atoms in the hydroxyapatite are substituted with magnesium atoms and a portion of phosphate groups are substituted with carbonate groups.

4 Claims, 3 Drawing Sheets

HYDROXYAPATITE, COSMETIC, FOOD, AND METHOD FOR PRODUCING THE SAME

CROSS-REFERENCE TO RELATED APPLICATIONS

This application is a Divisional Application of U.S. application Ser. No. 16/665,582 filed Oct. 28, 2019, which is a Continuation Application of PCT Application No. PCT/JP2017/016855, filed Apr. 27, 2017, the entire contents of which are incorporated herein by reference in their entireties.

BACKGROUND OF THE INVENTION

1. Field of the Invention

The present invention relates to hydroxyapatite, cosmetic and food, and a method for producing the same.

2. Description of the Related Art

Hydroxyapatite ($Ca_{10}(PO_4)_6(OH)_2$) is a weak alkaline calcium phosphate compound. Hydroxyapatite is used for artificial bones, artificial tooth roots, bone fillers, pharmaceutical carriers and the like because of its excellent biocompatibility. In recent years, hydroxyapatite has also been applied to cosmetics, foods and the like.

For example, a technique relating to a liquid or creamy cosmetic in which a hydroxyapatite colloidal fine particle solid having a particle size of 0.1 to 0.2 μm is dispersed in water or an organic solvent is disclosed in Patent Literature 1 (JP S62-195317 A).

In addition, a technique of producing a cosmetic containing 2 to 20 μm hydroxyapatite obtained by reacting calcium hydroxide and an aqueous phosphoric acid solution under alkaline conditions of pH 10 and drying the aqueous solution with a spray dryer is disclosed in Patent Literature (JP S63-096110 A).

Furthermore, a technique relating to magnesium-substituted crystalline hydroxyapatite with a stable and pure phase that contains approximately 2.0 to 29% magnesium and at least 75 wt % of the magnesium is replaced with calcium ions in the hydroxyapatite lattice structure, is disclosed in Patent Literature 3 (JP 2004-532172 A).

Moreover, a technique for synthesizing carbonate- and magnesium-substituted hydroxyapatite containing 0.028 to 0.826 wt % of magnesium and 0 to 6.83 wt % of carbonate ions is disclosed in Non-Patent Literature 1 (Materials Research. 2013; 16(4): 779-784).

BRIEF SUMMARY OF THE INVENTION

However, in the cosmetic producing process, a solution containing hydroxyapatite of primary particles is dried with a spray dryer or the like and hydroxyapatite is thereby aggregated and solidified to form large secondary particles. Since the density of hydroxyapatite is generally as high as 3.16 g/cm³, such hydroxyapatite tends to precipitate and does not disperse uniformly when added to cosmetics. For this reason, the cosmetic ingredients composition becomes various. Moreover, such hydroxyapatite is inferior in the adsorptivity on a lipid, protein, dirt, etc., and bioaffinity and absorptivity.

In addition, according to Patent Literature 3, hydroxyapatite containing approximately 2.0 to 29% magnesium is magnesium hydroxyapatite, and is different in physical and chemical properties from calcium hydroxyapatite having high biocompatibility. The ionic radius of magnesium is as small as approximately 70% of the ionic radius of calcium. For this reason, if the amount of magnesium contained in hydroxyapatite significantly exceeds 2 wt %, it is presumed that the crystal structure of hydroxyapatite may be distorted, the original properties of hydroxyapatite may be impaired, and bioaffinity may be adversely affected.

Furthermore, according to Non-Patent Literature 1, the size of the produced hydroxyapatite particles is as large as 63 to 90 μm.

The present invention has been accomplished in view of the above circumstances, and its object is to provide hydroxyapatite with improved bioaffinity, dispersibility, adsorptivity, absorptivity and cell activation ability, cosmetic and food containing the same, and a method for producing the same.

According to the present invention, there is provided carbonate- and magnesium-substituted hydroxyapatite having a part of calcium of the hydroxyapatite substituted with magnesium and a part of a phosphate group substituted with a carbonate group, and having a particle size of 5 nm or more and 60 nm or less.

According to the present invention, hydroxyapatite having a particle size of 5 nm or more and 60 nm or less and exhibiting higher bioaffinity, dispersibility, adsorptivity, absorptivity, and cell activation ability, cosmetic and food containing the same, and a method for producing the same, can be provided.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments will be described hereinafter with reference to the accompanying drawings.

1. Carbonate- and Magnesium-Substituted Hydroxyapatite

In the embodiments, carbonate- and magnesium-substituted hydroxyapatite is provided.

Carbonate- and magnesium-substituted hydroxyapatite is a compound in which a part of calcium of hydroxyapatite having the chemical formula $Ca_{10}(PO_4)_6(OH)_2$ is substituted with magnesium and a part of phosphate group is substituted with a carbonate group. The substitution rate of calcium with magnesium and the substitution rate of phosphate groups with carbonate groups is selected such that the particle size of carbonate- and magnesium-substituted hydroxyapatite is 5 nm or more and 60 nm or less (more preferably, the particle size is 10 nm or more and 50 nm or less). The particle size is an average value of the lengths of the short axis and the long axis direction of primary particles of carbonate- and magnesium-substituted hydroxyapatite. The primary particle refers to a particle generated by the growth of a single crystal nucleus.

For example, carbonate- and magnesium-substituted hydroxyapatite may be a compound represented by the chemical formula $((Ca, Mg)_{10}(PO_4, CO_3)_6(OH)_2)$ or $Ca_{10-x}Mg_x(PO_4)_{6-2/3y}(CO_3)_y(OH)_2$. It is desirable that x is any value from 0.005 to 0.5, and y is any value from 0.01 to 3.0. A more desirable x value is any value from 0.01 to 0.3, and a more desirable y value is any value from 0.02 to 1.0. In addition, examples of desirable carbonate- and magnesium-substituted hydroxyapatite are $Ca_{9.99}Mg_{0.01}(PO_4)_{5.98}(CO_3)_{0.02}(OH)_2$, $C_{9.7}Mg_{0.3}(PO_4)_{5.33}(CO_3)_1(OH)_2$ or a mixture of any of these.

Alternatively, carbonate- and magnesium-substituted hydroxyapatite is hydroxyapatite, in which calcium of hydroxyapatite having chemical formula $Ca_{10}(PO_4)_6(OH)_2$ is substituted with 0.03 wt % or more and 5 wt % or less of magnesium with respect to calcium, and a part of the phosphate groups is substituted with 0.2 wt % or more and 10 wt % or less of the carbonate group with respect to the phosphate group.

The carbonate- and magnesium-substituted hydroxyapatite of the embodiments may be present in the liquid. The formation and/or growth of secondary particles caused by drying is suppressed due to the presence in the liquid. The secondary particles are particles generated by coalescence growth, aggregation, consolidation, etc., of the primary particles. As a result, carbonate- and magnesium-substituted hydroxyapatite can be present in a smaller particle size. Examples of the liquid include water, an aqueous solution, emulsion, oil, cream, gel and the like.

The carbonate- and magnesium-substituted hydroxyapatite of the embodiments described above can easily be absorbed by the living body and have higher bioaffinity. In addition, it has a high effect of adsorbing lipids, proteins, dirt, bacteria, and odor-causing substances. Their effects are considered to result from the facts that carbonate- and magnesium-substituted hydroxyapatite have a smaller particle size compared to conventional hydroxyapatite, that it has a large surface area ratio to weight, that it has properties close to living tissue, and that its surface potential is more positively inclined. For example, the surface area of carbonate- and magnesium-substituted hydroxyapatite is 100 $m^2/g$ or more, which is ten times or more that of conventional hydroxyapatite.

Furthermore, carbonate- and magnesium-substituted hydroxyapatite of the embodiments has a high effect of activating cells. In general, it has been found that hydroxyapatite is effective in activation of cells such as promotion of collagen production in fibroblasts or promotion of metabolism in cells caused by attracting capillaries. Since the carbonate- and magnesium-substituted hydroxyapatite of the embodiments have a small particle size and are excellent in absorptivity and bioaffinity, they exhibit a more excellent cell activation effect.

In addition, the carbonate- and magnesium-substituted hydroxyapatite is uniformly dispersed when mixed with liquids, emulsions, oils, creams, gels and the like.

Therefore, the carbonate- and magnesium-substituted hydroxyapatite of the embodiments is excellent in bioaffinity, dispersibility, adsorptivity, absorptivity, and cell activation ability.

Such carbonate- and magnesium-substituted hydroxyapatite can be used by addition to, for example, cosmetics or foods described later, or pharmaceuticals, dental chemicals, kitchen detergents, laundry detergents, cleaning detergents, disinfectants, disinfectants, deodorants, fertilizers, agricultural chemicals, a liquid to be dispersed with a humidifier, or the like.

2. Method for Producing Carbonate- and Magnesium-Substituted Hydroxyapatite

In the embodiments, the method for producing carbonate- and magnesium-substituted hydroxyapatite mentioned above is provided.

Figure 1:
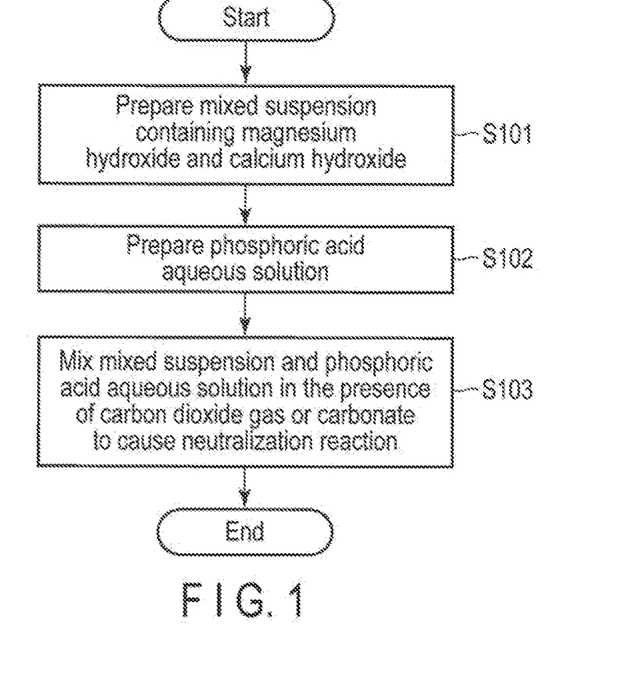
FIG. 1 is a flowchart illustrating a method for producing carbonate- and magnesium-substituted hydroxyapatite by neutralization reaction.

An example of the producing method of the embodiments is shown in FIG. 1. The producing method is a method for producing hydroxyapatite by neutralization reaction, comprising, for example, a step (S101) of preparing the mixed suspension containing magnesium hydroxide and calcium hydroxide, a step (S102) of preparing phosphoric acid aqueous solution, and a step (S103) of mixing the mixed suspension and the phosphoric acid aqueous solution in the presence of carbon dioxide or carbonate to cause the neutralization reaction.

In step S101, a mixed suspension containing magnesium hydroxide and calcium hydroxide is prepared. The mixed suspension contains an aqueous solution and solids of magnesium hydroxide and calcium hydroxide. The molar ratio of magnesium hydroxide to calcium hydroxide in the mixed suspension may be set such that carbonate- and magnesium-substituted hydroxyapatite having a desired substitution rate can be obtained. For example, the molar ratio of magnesium hydroxide to calcium hydroxide in the mixed suspension is desirably 1:1000 to 1:100, more desirably 1:500 to 1:50. A desirable concentration of magnesium hydroxide is 0.0002 to 0.01 mol/L, and a desirable concentration of calcium hydroxide is 0.05 to 1.0 mol/L. A temperature of the mixed suspension is desirably 5 to 50° C.

In step S102, an aqueous phosphoric acid solution is prepared. The molar ratio of magnesium hydroxide and calcium hydroxide contained in the mixed suspension to phosphoric acid, and the concentration of the phosphoric acid aqueous solution may be set so as to obtain carbonate- and magnesium-substituted hydroxyapatite having a desired substitution rate. A desirable concentration of the phosphoric acid aqueous solution is 0.03 to 0.6 mol/L. A temperature of the phosphoric acid aqueous solution is desirably 5 to 50° C.

In step S103, the mixed suspension obtained in step S101 and the phosphoric acid aqueous solution obtained in step S102 are mixed in the presence of carbon dioxide gas or carbonate to cause a neutralization reaction. For example, step S103 is performed by mixing the mixed suspension and the phosphoric acid aqueous solution in a carbon dioxide gas atmosphere. Alternatively, a carbonate may be added in advance to the mixed suspension or the phosphoric acid aqueous solution, and both may be mixed. Alternatively, carbonate may be added to the mixture obtained by mixing the mixed suspension and the phosphoric acid aqueous solution.

The carbon dioxide gas may be a gas containing carbon dioxide, and pure carbon dioxide gas or air may be used as the carbon dioxide gas. As the carbonate, for example, ammonium carbonate, sodium bicarbonate, sodium carbonate, potassium carbonate, or potassium bicarbonate can be used. The concentrations of carbon dioxide and carbonate are, for example, 0.03 to 0.1 mol/L and 0.01 to 1.0 mol/L, respectively.

Mixing may be performed by, for example, stirring. Stirring may be performed by, for example, a stirring device known to a person skilled in the art, such as a stirrer, but is desirably performed using an ultrasonic vibration device. When an ultrasonic vibration device is used, the output of the device varies depending on the scale of mass production, but stirring can be performed at an intensity in the range of 100 W to 2 kW and 10 to 50 kHz. Aggregation of hydroxyapatite crystals caused by the neutralization reaction can be thereby prevented. As a result, carbonate- and magnesium-substituted hydroxyapatite having a smaller particle size can be obtained. In addition, when the carbon dioxide gas is used, the phosphoric acid group can be more efficiently replaced with the carbonate group, by stirring with the strength within the above range.

By the neutralization reaction, a suspension containing carbonate- and magnesium-substituted hydroxyapatite can be obtained. After the neutralization reaction, the suspension may be concentrated. Alternatively, a part of the suspension precipitate may be removed.

By performing steps S101 to S103 described above, carbonate- and magnesium-substituted hydroxyapatite having a particle size of 5 nm or more and 60 nm or less can be obtained.

Figure 2:
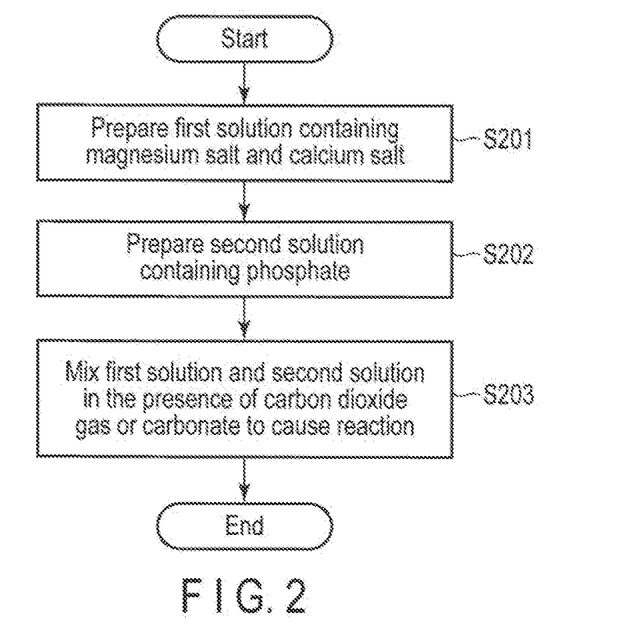
FIG. 2 is a flowchart illustrating a method for producing carbonate- and magnesium-substituted hydroxyapatite by a reaction between two salts.

An example of a producing method in a further embodiment is shown in FIG. 2. This producing method is a method for producing hydroxyapatite by reaction between two salts, comprising a step (S201) of preparing a first solution containing a magnesium salt and a calcium salt, a step (S202) of preparing a second solution containing a phosphate, and a step (S203) of mixing the first solution and the second solution in the presence of carbon dioxide gas or carbonate to cause the reaction.

In step S201, the first solution containing a magnesium salt and a calcium salt is prepared. As the magnesium salt, for example, magnesium chloride, magnesium nitrate, magnesium sulfate, or magnesium acetate can be used, but using magnesium chloride is desirable since it is inexpensive. As the calcium salt, calcium nitrate, calcium chloride, calcium lactate, or the like can be used, but using calcium chloride is desirable since it is inexpensive.

A molar ratio of calcium salt to calcium salt in the first solution may be set so as to obtain carbonate- and magnesium-substituted hydroxyapatite having a desired substitution rate. For example, the molar ratio of magnesium salt to calcium salt in the first solution is desirably 1:1000 to 1:100, more desirably 1:500 to 1:50. A desirable magnesium salt concentration is 0.0002 to 0.01 mol/L, and a desirable calcium salt concentration is 0.05 to 1.0 mol/L. A temperature of the first solution is desirably 5 to 50° C.

In step S202, a second solution containing phosphate is prepared. As the phosphate, ammonium phosphate, disodium hydrogen phosphate, dipotassium hydrogen phosphate, or the like can be used, but using ammonium phosphate is desirable since ammonia is volatilized and does not remain.

The molar ratio of magnesium salt and calcium salt to phosphate contained in the first solution, and the concentration of phosphate may be set so as to obtain carbonate- and magnesium-substituted hydroxyapatite having a desired substitution rate. A desirable phosphate concentration is 0.03 to 0.6 mol/L. A temperature of the phosphoric acid aqueous solution is desirably 5 to 50° C.

In step S203, the first solution obtained in step S201 and the second solution obtained in step S202 are mixed in the presence of carbon dioxide or carbonate to cause a salt-salt reaction. For example, step S203 is performed by mixing the first solution and the second solution in a carbon dioxide gas atmosphere. Alternatively, carbonate may be added in advance to the first solution or the second solution, and both may be mixed. Alternatively, carbonate may be added to the mixture of the first solution and the second solution.

As the carbon dioxide gas and carbonate, for example, the same carbon dioxide gas and carbonate as described above can be used. Mixing may be performed by the method described above.

By the salt-salt reaction, a suspension containing carbonate- and magnesium-substituted hydroxyapatite is obtained. After the reaction, the suspension may be concentrated. Alternatively, a part of the suspension precipitate may be removed.

By performing steps S201 to S203 described above, carbonate- and magnesium-substituted hydroxyapatite having a particle size of 5 nm or more and 60 nm or less can be obtained.

Carbonate- and magnesium-substituted hydroxyapatite having a particle size of 5 nm or more and 60 nm or less can be obtained by the method of the embodiment described above, for the following reasons. For example, since magnesium atoms are smaller than calcium atoms, the size of the molecule itself can be made smaller by replacing calcium with magnesium. In addition, substituted carbonate group suppresses crystal growth. Furthermore, formation of large secondary particles can be prevented by not drying the suspension after the neutralization reaction in step S103 or the salt-salt reaction in step S203.

Therefore, according to the present invention, hydroxyapatite excellent in bioaffinity, dispersibility, adsorptivity, absorptivity, and cell activation ability, can be produced.

Moreover, according to the producing method of the embodiment, since hydroxyapatite does not need to be synthesized under alkaline conditions as in the prior art, excess alkali is not contained in the obtained crystal. For this reason, the carbonate- and magnesium-substituted hydroxyapatite produced by the producing method does not cause irritation or damage when brought into contact with a living body. For example, cosmetics containing carbonate- and magnesium-substituted hydroxyapatite described later do not cause irritation or damage to the skin tissue by alkali.

3. Cosmetic

According to a further embodiment, a cosmetic comprising carbonate- and magnesium-substituted hydroxyapatite having a particle size of 5 nm or more and 60 nm or less is provided.

The carbonate- and magnesium-substituted hydroxyapatite contained in the cosmetic is carbonate- and magnesium-substituted hydroxyapatite having any one of the above-mentioned particle sizes of 5 nm or more and 60 nm or less. For example, such hydroxyapatite may be produced by the above producing method.

The cosmetic may be any known cosmetic, for example, a mixture of materials selected from purified water, other liquids, oil, soap base, alcohol such as ethanol or glycerin, fragrance, stearic acid, squalene, propylene glycol, petrolatum, surfactant, paraffin, various vitamins, collagen and the like. Such a cosmetic includes, for example, hair shampoo, rinse, conditioner, treatment, rinse-in shampoo, body shampoo, hand shampoo, facial cleansing foam, cleansing emulsion, cleansing cream, cleansing oil, soap, liquid soap, liquid bath agent, lotion, cosmetic liquid, cosmetic oil, emulsion, cream, gel, toothpaste powder, toothpastes, mouthwash, whitening liquid deodorant, or the like, but is not limited to these. In particular, since carbonate- and magnesium-substituted hydroxyapatite is better adsorbed with lipids and oils such as oleic acid, oleyl oleate, and olive oil, the cosmetic desirably contains them. In addition, when containing vitamin C, hydroxyapatite amplifies the antioxidant power of vitamin C, and thus can provide a cosmetic with a higher skin quality improving effect.

A concentration of carbonate- and magnesium-substituted hydroxyapatite in the cosmetic is desirably, for example, 0.001 wt % or more and 15 wt % or less.

Since carbonate- and magnesium-substituted hydroxyapatite has a small particle size as described above, it easily enters pores and epidermis, and has a high effect of adsorbing proteins, lipids, dirt, bacteria, or substances that cause odor. For this reason, by using the cosmetic, sebum, keratin plugs, darkening, keratin and the like of skin can be efficiently removed, and acne, athlete's foot, worm odor, aging odor and the like can be prevented and improved. In addition, as described above, carbonate- and magnesium-substituted hydroxyapatite promotes collagen production in fibroblasts, and promotes cell metabolism by attracting capillaries. Based on these matters, skin quality and hair quality can be further improved by using the cosmetics. In addition, since the hydroxyapatite mentioned here has a small particle size and hardly gives physical irritation to the skin, the cosmetic feeling is smoother. Furthermore, if the hydroxyapatite contained in the cosmetic is produced by the above producing method, it does not cause irritation and damage to the skin due to alkali.

When the cosmetic is toothpaste, toothpaste, mouthwash, whitening solution, or the like, the cosmetic has a high effect of adsorbing and removing tooth dirt, mutans bacteria, plaque and the like. In addition, carbonate- and magnesium-substituted hydroxyapatite has a high effect of supplementing minerals in the decalcified subsurface portion of the tooth enamel that is dissolved by the acid generated by bacteria in the plaque or the acid of food and drink. This is considered to result from the fact that the size, composition and structure of the carbonate- and magnesium-substituted hydroxyapatite are similar to those of the hydroxyapatite contained in the teeth. Therefore, by using the cosmetic, it is possible to fill and repair the damages on the tooth surface, remineralize the initial caries, and smooth the surface to prevent adhesion of plaque, dirt and the like.

Moreover, since the carbonate- and magnesium-substituted hydroxyapatite is uniformly dispersed to the material, the cosmetic uniformly containing the ingredients is provided.

4. Method for Producing Cosmetic

According to the embodiment, a method for manufacturing the cosmetic is provided.

Figure 3:
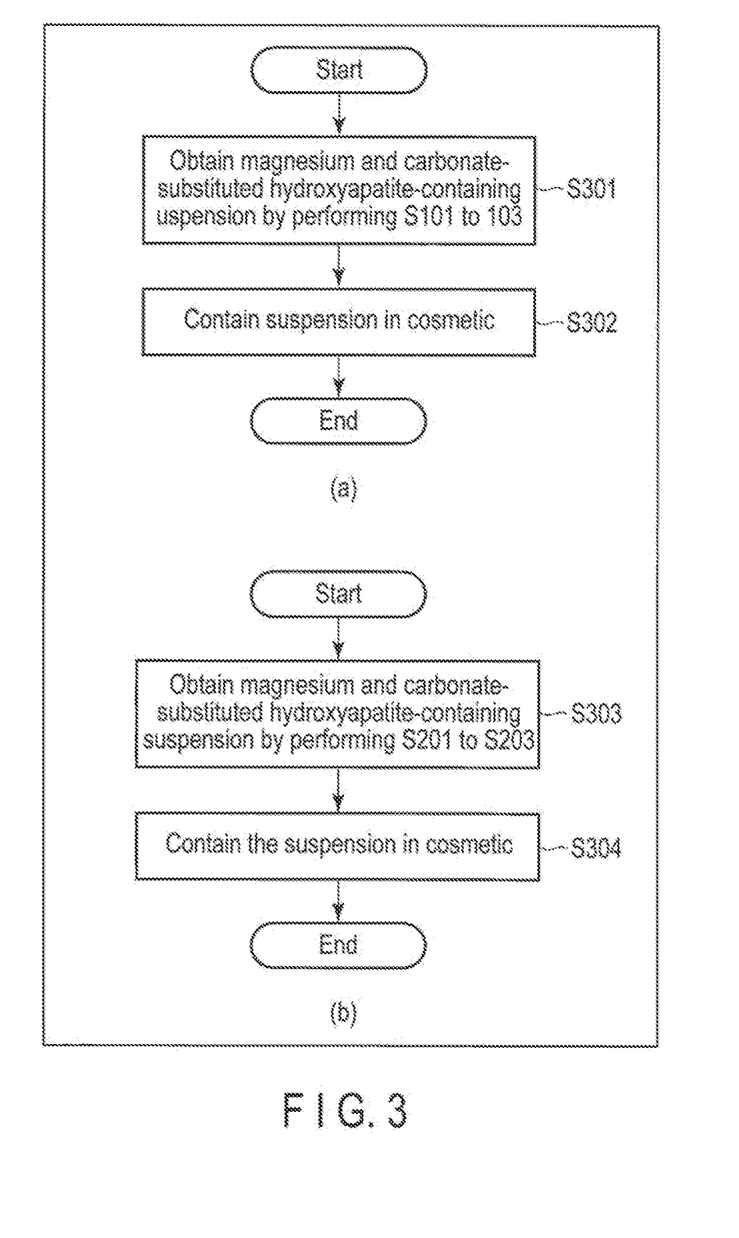
FIG. 3 is a flowchart illustrating a method for producing cosmetics containing carbonate- and magnesium-substituted hydroxyapatite.

Part (a) and (b) of FIG. 3 show an example of a method for producing the cosmetic. The method for producing the cosmetic includes a step (S301) of obtaining a carbonate- and magnesium-substituted hydroxyapatite-containing suspension by executing S101 to S103 of the above method for producing the carbonate- and magnesium-substituted hydroxyapatite, and a step (S302) of containing the carbonate- and magnesium-substituted hydroxyapatite-containing suspension in the cosmetic ((a) of FIG. 3). Alternatively, the method of manufacturing the cosmetic includes a step (S303) of obtaining carbonate- and magnesium-substituted hydroxyapatite-containing suspension by performing S201 to S203 of the above method for producing the carbonate- and magnesium-substituted hydroxyapatite, and a step (S304) of containing the carbonate- and magnesium-substituted hydroxyapatite-containing suspension in the cosmetic ((b) of FIG. 3).

Step S301 and step S303 are the same as those of the above-described "2. Method for Producing Carbonate- and Magnesium-Substituted Hydroxyapatite". In step S302 and step S304, the carbonate- and magnesium-substituted hydroxyapatite-containing suspension is made to be contained in the cosmetic. Step S302 and step S304 may be performed, for example, by adding the suspension to any one of the above-described cosmetics produced in advance and mixing, or by producing cosmetic from raw materials of any cosmetics to which the suspension is added. Method for mixing may be selected depending on the type of cosmetic, and mixing can be performed by, for example, a mixer, a kneader, a stirrer, a disperser, a mixing device or the like.

According to the cosmetic producing method of the embodiment, carbonate- and magnesium-substituted hydroxyapatite can be contained in the cosmetic without drying. Cosmetics containing carbonate- and magnesium-substituted hydroxyapatite having a small particle size which are not aggregated and/or solidified can be thereby provided.

5. Food

According to a further embodiment, food containing carbonate- and magnesium-substituted hydroxyapatite is provided.

The carbonate- and magnesium-substituted hydroxyapatite contained in the foods is any of the above-described carbonate- and magnesium-substituted hydroxyapatite. For example, such hydroxyapatite may be produced by the above producing method.

The foods are, for example, beverages such as water, coffee, tea, fruit juice, and soft drinks, dairy products such as milk, yogurt and cheese, cooking oils such as salad oil and olive oil, seasonings, ice creams, soups, and cooked foods (retort foods), pet foods or supplements, but are not limited thereto. Furthermore, the foods may contain additives such as vitamins, and particularly desirably contain vitamin D and vitamin C. When containing vitamin D, the absorption efficiency of calcium is promoted. Therefore, such foods are particularly suitable for sports drinks, and are highly effective in preventing and improving osteoporosis and the like. In addition, since vitamin D is activated by hydroxyapatite, foods having a high absorption efficiency of vitamin D can be provided. In the case of containing vitamin C, hydroxyapatite amplifies the antioxidant power of vitamin C, and therefore can provide foods having a higher antioxidant power.

The concentration of carbonate- and magnesium-substituted hydroxyapatite in the food is, for example, 0.001 wt % or more and 10 wt % or less.

Since the carbonate- and magnesium-substituted hydroxyapatite of the embodiment has a small particle size and high absorptivity, it is efficiently absorbed from the stomach and intestine. For this reason, magnesium, calcium, and phosphoric acid can be ingested more efficiently by ingesting the foods. Furthermore, since the carbonate and magnesium-substituted hydroxyapatite is similar in composition to the inorganic components contained in bones and teeth, the foods are more effective in strengthening bone quality. In addition, since the carbonate- and magnesium-substituted hydroxyapatite of the embodiment can be uniformly dispersed in the foods, the foods that uniformly contain ingredients are provided.

6. Method for Producing Food

According to the embodiment, a method for producing the above foods is provided.

Figure 4:
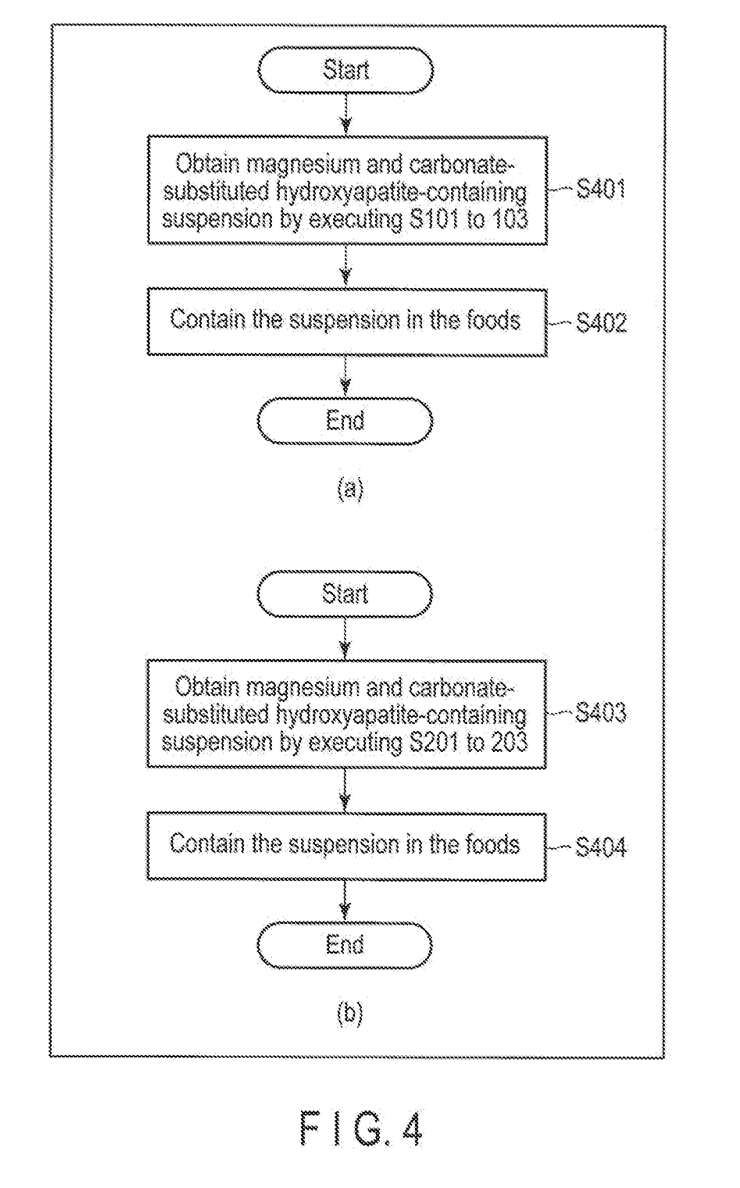
FIG. 4 is a flowchart illustrating a method for producing foods containing carbonate- and magnesium-substituted hydroxyapatite.

The examples of the method for producing the foods are shown in (a) and (b) of FIG. 4. The method for producing the foods includes a step (S401) of obtaining carbonate- and magnesium-substituted hydroxyapatite-containing suspension by executing S101 to S103 of the above method for producing the carbonate- and magnesium-substituted hydroxyapatite, and a step (S402) of containing the carbonate- and magnesium-substituted hydroxyapatite-containing suspension in the foods ((a) of FIG. 4). Alternatively, the method for producing the foods includes a step (S403) of obtaining carbonate- and magnesium-substituted hydroxyapatite-containing suspension by executing S201 to S203 of the above method for producing the carbonate- and magnesium-substituted hydroxyapatite, and a step (S404) of containing the carbonate- and magnesium-substituted hydroxyapatite-containing suspension in the foods ((b) of FIG. 4).

Step S401 or step S402 is the same as that of the above-described "2. Method for Producing Carbonate- and Magnesium-Substituted Hydroxyapatite". In step S402 or step S404, the carbonate- and magnesium-substituted hydroxyapatite-containing suspension is made to be contained in the foods. Step S402 or S404 may be performed, for example, by adding the suspension to any one of the above-described foods produced in advance and mixing, or by producing foods from raw materials of any foods to which the suspension is added. Mixing may be selected depending on the type of foods, and can be performed by, for example, a mixer, a kneader, a stirrer, a disperser, a mixing device or the like.

According to the food producing method of the embodiment, carbonate- and magnesium-substituted hydroxyapatite can be contained in the foods without drying. Foods containing carbonate- and magnesium-substituted hydroxyapatite with a small particle size which are not aggregated and/or solidified can be thereby provided.

Examples of the present invention will be described hereinafter in detail.

Example 1

A 1 L suspension containing 0.001 mol and 0.01 mol magnesium hydroxide and 0.1 mol and 1 mol calcium hydroxide in water at 22° C. and 37° C. was prepared. Next, a 1 L aqueous solution containing 0.06 mol to 0.6 mol of phosphoric acid at 22° C. and 37° C. was prepared. The suspension and aqueous solution at 22° C. and the suspension and aqueous solution at 37° C. were stirred and suspended in an atmosphere of carbon dioxide (air) using an ultrasonic agitator set at intensity of 600 W and 20 kHz, respectively, to obtain suspensions.

When the obtained suspensions were analyzed by X-ray diffraction (XRD), a typical hydroxyapatite crystal pattern was observed in each of the suspensions. That is, it was confirmed that the basic structure of the particles contained in the obtained suspensions is the same as that of hydroxyapatite.

Furthermore, when the obtained suspensions were analyzed by Fourier Transform Infrared Spectroscopy (FTIR), absorption peaks appeared in hydroxyl groups and carbonate groups. That is, it was confirmed that hydroxyapatite containing carbonic acid was synthesized.

In addition, as a result of analyzing the obtained suspensions by Inductively Coupled Plasma (ICP), it was confirmed that the particles contained in the obtained suspensions contained approximately 0.03 to 0.9 wt % of magnesium and approximately 0.5 to 5 wt % of carbonate ions. The weight percent of the substituted magnesium and carbonate ions was calculated by converting the molecular weight of hydroxyapatite to 1 kg.

It was confirmed from the analysis results of XRD, FTIR, and ICP described above that the obtained suspensions contained carbonate- and magnesium-substituted hydroxyapatite.

As a result of calculating the crystallite size of the microcrystal obtained by synthesis from the half-value width of the X-ray diffraction method, the size of the C axis (long axis direction) and A axis (short axis direction) of crystallite, i.e., the average primary particle size was widely distributed at 10 m or more and 60 nm or less. As the amount of magnesium and carbonate ion substitution was greater, the primary particle size was smaller and close to the minimum value of 10 nm.

The sedimentation of the suspensions obtained by the synthesis was slower as the size of the primary particles and the size of the secondary particles were smaller. In addition, no precipitation of crystals was observed from the supernatant fluid of the suspensions. That is, it was confirmed that the carbonate- and magnesium-substituted hydroxyapatite contained in the supernatant fluid contained floating microcrystals.

When the surface area of the obtained particles was measured by a gas adsorption method (BET method), the surface area was in the range of 50 $m^2/g$ to 120 $m^2/g$. The surface area was inversely proportional to the size of the primary particles. In contrast, the surface area of commercially available hydroxyapatite powder is 10 $m^2/g$ or less.

<Evaluation of Adsorptivity of Lipid (1)>

A first column filled with the powder of particles of Example 1 obtained by synthesis at room temperature of 22° C. and a second column filled with commercially available hydroxyapatite powder were prepared, and olive oil diluted with normal hexane was passed through each of the first column and the second column. After that, the first column and the second column were washed with normal hexane, and the amount of lipid peroxide contained in each of the washing solutions was measured. This experiment was performed five times, and the average value of the amount of lipid peroxide adsorbed was calculated by the iodine titration method. As a result, assuming that the adsorption amount of lipid peroxide contained in the washing solution of the first column was 100, the adsorption amount of lipid peroxide contained in the second column was in the range of 60 to 70. That is, it was confirmed that carbonate- and magnesium-substituted hydroxyapatite adsorbs more lipids than normal hydroxyapatite.

<Evaluation of Adsorptivity of Lipid (2)>

Suspension containing 1 wt % of commercially available hydroxyapatite crystals, 1 wt % of carbonate- and magnesium-substituted hydroxyapatite suspension obtained in Example 1, 1 wt % of α-alumina-containing purified water suspension, and 1 wt % of sericite-containing purified water suspension were prepared at 100 mL each. 5 g of oleic acid, oleyl oleate, and olive oil were added to each of the suspensions and immersed for 24 hours. After that, each suspension was washed with diethyl ether, and the amounts of adsorbed oleic acid, oleyl oleate and olive oil were analyzed by gravimetric analysis. As a result, assuming that the lipid adsorption amount of the suspension containing carbonate- and magnesium-substituted hydroxyapatite obtained in Example 1 is 1, the lipid adsorption amount of the suspension containing commercially available hydroxyapatite was approximately 0.8. In addition, the result that an (X-alumina containing purified water suspension and a sericite containing purified water suspension hardly adsorb a lipid was obtained.

<Evaluation of Dispersibility>

The carbonate- and magnesium-substituted hydroxyapatite suspension of Example 1 and commercially available hydroxyapatite powder were added to 100 g of commercially available cosmetics such as emulsions, cleansing creams, creams, and soaps, or commercially available foods such as drinking water, yogurt and juice so as to be 0.1 to 10 wt %.

As a result of observing the obtained cosmetics and foods, the carbonate- and magnesium-substituted hydroxyapatite contained in these cosmetics and foods and obtained in Example 1 had less precipitates and were well dispersed as compared with commercially available hydroxyapatite.

Example 2: Production and Evaluation of Lotion

An alkaline lotion (1000 mL in total) containing 3 g of potassium hydroxide, 1 g of carbonate and magnesium-substituted hydroxyapatite of Example 1, 200 mL of glycerin, 250 mL of ethanol, and 550 mL of purified water was prepared.

Ten adult male and female subjects used the lotion and lotion produced by replacing carbonate- and magnesium-substituted hydroxyapatite with 1 g of commercially available hydroxyapatite (α-alumina or sericite) in the above composition, and compared the effect of removing dirt and the feeling of use. As a result, eight of ten subjects had an impression that the skin lotion containing the carbonate- and magnesium-substituted hydroxyapatite had the lowest lipid and had a refreshing feeling.

Example 3: Production and Evaluation of Cream

Cream (100 g) containing 10 to 20 wt % of stearic acid, 0.5 to 1.0 wt % of potassium hydroxide, 10 to 20 wt % of glycerin, 0.5 to 1.0 wt % of perfume, 5 to 10 wt % of carbonate- and magnesium-substituted hydroxyapatite of Example 1, an appropriate amount of an antioxidant, a bactericidal antibacterial agent and purified water was produced. As a result of visual observation of the hydroxyapatite dispersed in the cream, hydroxyapatite was well dispersed.

The cream and a cream produced by replacing carbonate- and magnesium-substituted hydroxyapatite of the above composition with commercially available hydroxyapatite were applied to faces of ten subjects including five males and five females and then washed. As a result, all the subjects had an impression that the cream containing the carbonate- and magnesium-substituted hydroxyapatite was smoother and had a refreshing feeling after washing.

Example 4: Production and Evaluation of Water Soap 1 to 5% of carbonate- and magnesium-substituted hydroxyapatite suspension of Example 1 was added to 30% aqueous solution of temporary soap obtained by saponifying fats and oils such as vegetable oil with potassium hydroxide, and a thickening binder and a moisturizing component were blended to obtain an appropriate viscosity, and liquid soap was thereby produced.

Ten adult male and female subjects used the liquid soap and the liquid soap produced by replacing the carbonate- and magnesium-substituted hydroxyapatite of the above composition with commercially available hydroxyapatite, and compared the effect of removing dirt and feeling of use. As a result, seven persons had an impression that the liquid soap with the addition of carbonate- and magnesium-substituted hydroxyapatite removed dirt better and had a refreshing feeling of use after use.

Example 5: Method for Producing Bath Agent

A bath agent containing 10 g of 1 wt % carbonate- and magnesium-substituted hydroxyapatite suspension of Example 1, purified water 90 g, sake 10 g, natural salt 1 g, citric acid 50 g, potato starch 50 g, jojoba oil 2 g, and 1 g of cypress essential oil was produced.

Ten adult male and female subjects put 20 g of the above bath agent into a 200 L bathtub and bathed. When the bath agent was compared with a bath agent produced by replacing the carbonate- and magnesium-substituted hydroxyapatite of the above composition with commercially available hydroxyapatite, eight of ten subjects had an impression that the bath agent to which the carbonate- and magnesium-substituted hydroxyapatite were added had less sediment and was excellent in fluidity. In addition, there was also an impression that the skin surface was smoothed by removing dirt and keratin from the skin surface.

Example 6: Production and Evaluation of Yogurt

Yogurt was produced by adding 10 mL of 0.1 wt % carbonate- and magnesium-substituted hydroxyapatite suspension of Example 1 to 100 g of commercially available yogurt.

As a result of visual observation of the carbonate- and magnesium-substituted hydroxyapatite contained in the yogurt, neither aggregation nor precipitation occurred, and hydroxyapatite was well dispersed.

Example 7: Production and Evaluation of Orange Juice

An orange juice was produced by adding 10 mL of 0.1 wt % carbonate- and magnesium-substituted hydroxyapatite suspension of Example 1 to 90 g of commercially available 100% orange juice. The taste of the orange juice produced was equivalent to the taste of commercial orange juice before adding the carbonate- and magnesium-substituted hydroxyapatite suspension.

Example 8: Production and Evaluation of Calcium Supplementing Drinking Water

Calcium supplemented drinking water was produced by adding 1 mL of a 1%-suspended carbonate- and magnesium-substituted hydroxyapatite suspension of Example 1 to 100 g of 0.1% saline solution. When the calcium supplemented drinking water and calcium supplemented drinking water produced by replacing carbonate- and magnesium-substituted hydroxyapatite of the above composition with commercially available hydroxyapatite were visually observed and compared, the commercially available hydroxyapatite powder was precipitated and aggregated, but the carbonateand magnesium-substituted hydroxyapatite were well dispersed without precipitation or aggregation.

In addition, the bending strength of a femur of a mouse that have been given this calcium-supplemented drinking water every day for 3 months was greater by approximately 20% than the bending strength of a mouse that have been supplied with additive-free drinking water every day for 3 months.

Example 9

A 1 L aqueous solution containing 0.1 mol magnesium chloride and 0.1 mol calcium nitrate was prepared. A 1 L aqueous solution containing 0.06 mol of ammonium phosphate was prepared. Both of the aqueous solutions were stirred with an ultrasonic stirring device adjusted at 37° C. and set at 600 W and 20 kHz strength in a carbon dioxide (air) atmosphere to obtain a suspension.

As a result of analyzing the obtained suspension by XRD, FTIR, and ICP in the same manner as in Example 1, it was confirmed that approximately 0.5 wt % magnesium and approximately 2 wt % carbonate ions were contained in the suspension. In addition, it was confirmed that the suspension was a suspension of approximately 0.5 wt % of carbonate- and magnesium-substituted hydroxyapatite crystals.

Example 10

A 1 L aqueous solution containing 0.025 mol sodium bicarbonate and 0.25 mol calcium salt was prepared. 15 g of 85% aqueous phosphoric acid solution was prepared. A calcium hydroxide aqueous solution and phosphoric acid were stirred using an ultrasonic stirring device set to a strength of 37° C., 600 W, and 20 kHz to obtain a suspension.

As a result of analyzing the obtained suspension by XRD, FTIR, and ICP in the same manner as in Example 1, it was confirmed that 0.2 wt % magnesium and approximately 5 wt % carbonate ions were contained in the suspension. In addition, it was confirmed that the microcrystals were carbonate- and magnesium-substituted hydroxyapatite crystals. Furthermore, the size of primary particles of the carbonate- and magnesium-substituted hydroxyapatite microcrystals obtained was 20 nm or less.

When the adsorptivity and dispersibility of the carbonate- and magnesium-substituted hydroxyapatite obtained in Examples 9 and 10 were evaluated by the methods described above, the same results as those of Example 1 were obtained. In addition, when the carbonate- and magnesium-substituted hydroxyapatite of Examples 9 and 10 was used to be applied to Examples 2 to 8 instead of the carbonate- and magnesium-substituted hydroxyapatite of Example 1, the same results as those of the case using the carbonate- and magnesium-substituted hydroxyapatite of Example 1 were obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for producing a suspension comprising carbonate- and magnesium-substituted hydroxyapatite having a part of calcium substituted with magnesium and a part of phosphate group substituted with a carbonate group, and comprising primary particles in a non-aggregated state, the primary particles having a particle size of 5 nm or more and 60 nm or less,
the method comprising:
preparing a mixed suspension comprising magnesium hydroxide and calcium hydroxide;
preparing a phosphoric acid aqueous solution; and
mixing the mixed suspension and the phosphoric acid aqueous solution by stirring in the presence of pure carbon dioxide gas, causing a neutralization reaction, and obtaining, in a liquid state, the suspension comprising the carbonate- and magnesium-substituted hydroxyapatite comprising the primary particles in the non-aggregated state.

2. A method for producing a suspension comprising carbonate- and magnesium-substituted hydroxyapatite having a part of calcium substituted with magnesium and a part of phosphate group substituted with a carbonate group, and comprising primary particles in a non-aggregated state, the primary particles having a particle size of 5 nm or more and 60 nm or less,
the method comprising:
preparing a first solution comprising magnesium salt and calcium salt;
preparing a second solution comprising phosphate salt; and
mixing the first solution and the second solution by stirring in the presence of pure carbon dioxide gas, causing a reaction, and obtaining, in a liquid state, the suspension comprising the carbonate- and magnesium-substituted hydroxyapatite comprising the primary particles in the non-aggregated state.

3. The method of claim 1, wherein the stirring is executed with an ultrasonic vibration device.

4. The method of claim 2, wherein the stirring is executed with an ultrasonic vibration device.

* * * * *